United States Patent [19]

Gnuechtel

[11] 4,186,309
[45] Jan. 29, 1980

[54] WEB MONITORING AND CONTROL APPARATUS FOR WEB HANDLING MACHINERY

[75] Inventor: Herman C. Gnuechtel, Chicago, Ill.

[73] Assignee: Web Printing Controls Co. Inc., Bensenville, Ill.

[21] Appl. No.: 841,901

[22] Filed: Oct. 13, 1977

[51] Int. Cl.² ............................................. G01N 21/30
[52] U.S. Cl. ....................................... 250/561; 28/187; 57/81; 242/57; 250/572
[58] Field of Search ................. 28/187; 57/81; 66/161; 139/273 A; 242/57, 75, 52; 250/561, 562, 571, 572, 548

[56] References Cited

U.S. PATENT DOCUMENTS

| | | | |
|---|---|---|---|
| 2,451,816 | 10/1948 | Dunn | 250/561 X |
| 3,906,232 | 9/1965 | Meihofer | 250/571 X |

Primary Examiner—Lawrence J. Dahl
Attorney, Agent, or Firm—Fitch, Even & Tabin

[57] ABSTRACT

An improved web monitoring and control apparatus is disclosed for use with web handling machinery, such as printing presses and the like which are of the type that have a generally continuous web of material being printed or otherwise processed. The apparatus directs modulated infrared energy onto the web and detects the reflection of the energy from the web. The apparatus detects the occurrence of a web break and shuts down the machinery. The apparatus includes an automatic arming control which activates the apparatus when the machinery moves the web at some preselected percentage of its total speed and also includes apparatus for detecting when the detector lens has become soiled and provides a warning to the operators that conditions are approaching which may result in a false web break detection which would shut down the machinery.

12 Claims, 3 Drawing Figures

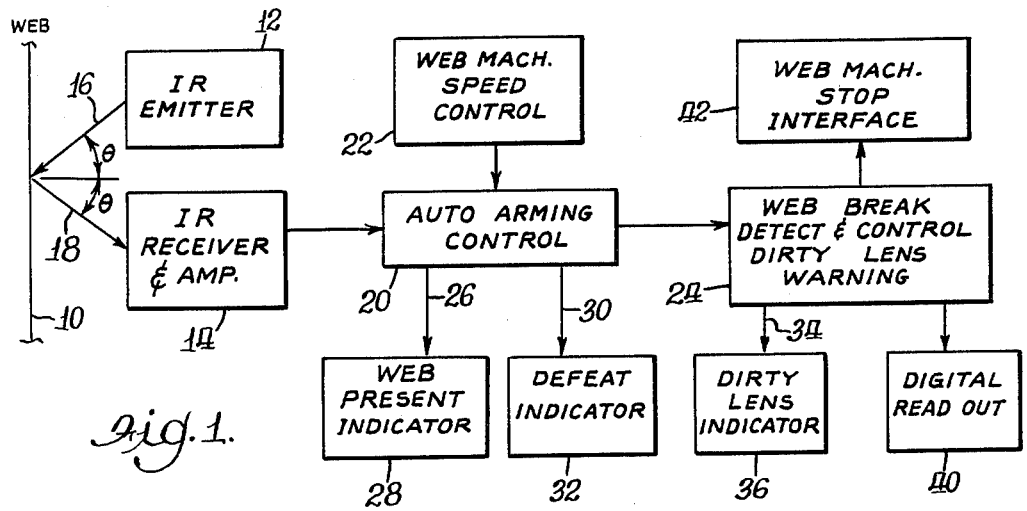
Fig. 1.
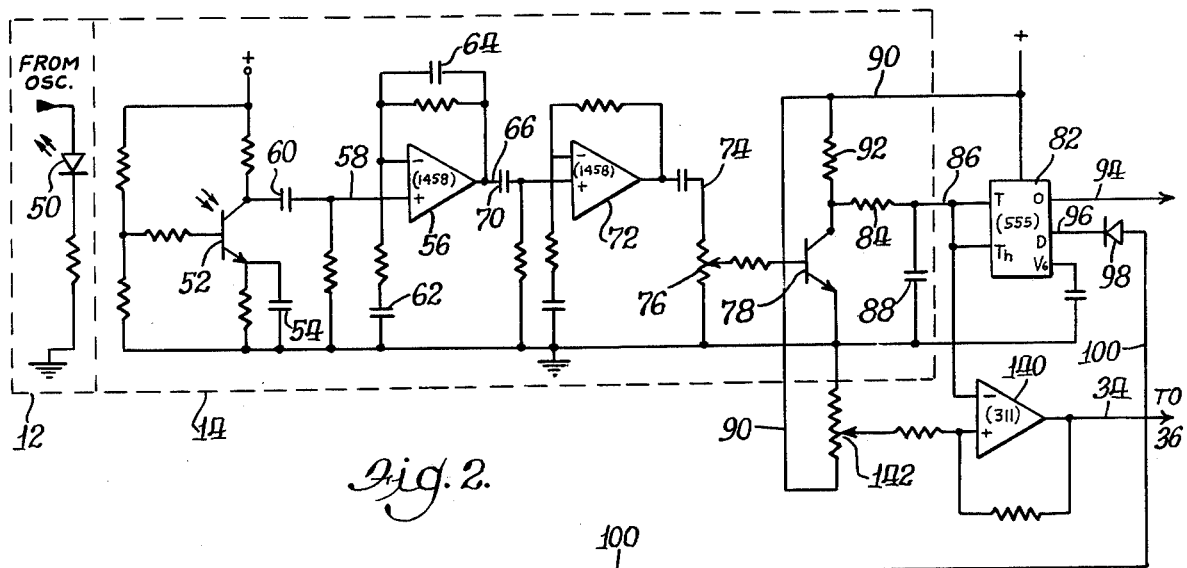
Fig. 2.
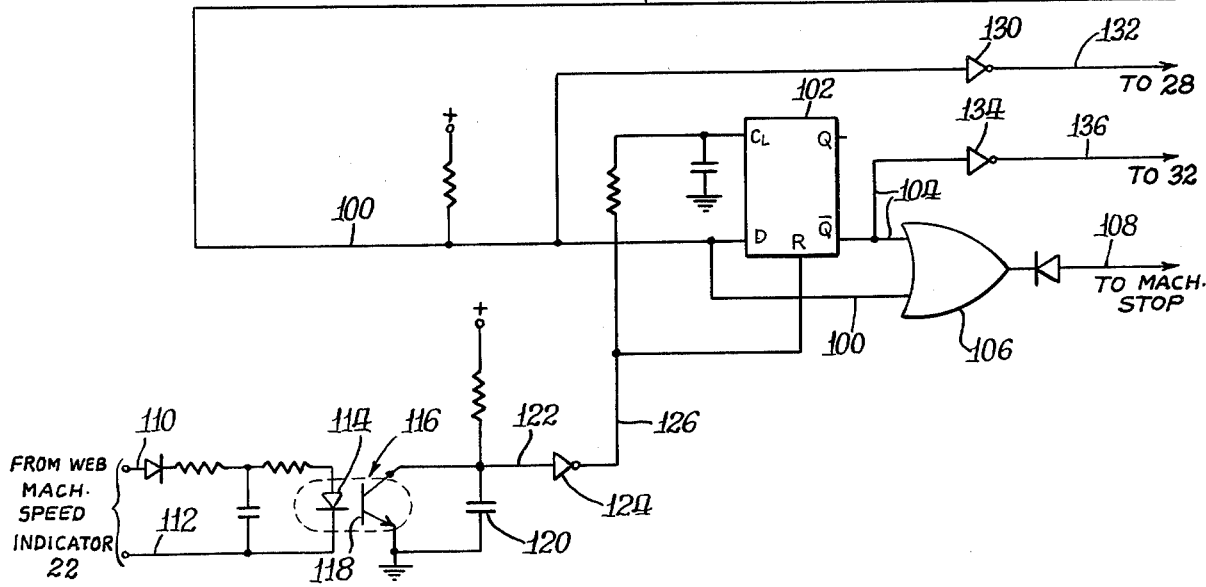

WEB MONITORING AND CONTROL APPARATUS FOR WEB HANDLING MACHINERY

The present invention relates to an improved web monitoring and control apparatus for use with web handling machinery such as printing presses or the like which handle a generally continuous, moving web.

There are many industries which utilize machinery that handles a generally continuous, moving web of material that may be relatively strong, such as fabric, some plastic films, metal foil and the like. However, other web materials may be inherently quite weak, such as various grades of paper, than plastic films and the like. In printing presses, for example, the breakage of a web of paper being printed can cause severe damage to the press, usually due to the broken web winding up on one of the press rolls which rapidly increases its size and produces staggering stresses on the press structure which ultimately breaks. Monitoring devices of many kinds have been developed to detect breaks in webs, such as physical contact switches and the like, which then shut down the web handling apparatus before damage can occur.

Recent improvements in web monitoring systems have included photoelectric circuits which essentially use a light source and receiver located on the same side of the web, with the receiver detecting reflected light from the web when the web is present. There have also been systems which utilize infrared energy wherein the infrared source is intermittently excited at a low frequency, i.e., about 100 Hertz, in an effort to exclude ambient light from creating a false web present indication. Since the detectors receive the reflected light from the light source, a problem can occur when the web being monitored is one in which the reflected light is quite low, as for example in the printing of newspapers which often have dark areas due to a heavy amount of printing and the reflected light from the blackened areas is considerably reduced. Moreover, the lenses of detector units will often become soiled due to the accumulation of dust and ink and the levels of light will be gradually reduced, increasing the likelihood of a false web break indication being generated.

Another problem with many systems is that they must be manually activated by the operators who control the web handling machinery and a continuing problem is that they either forget to activate them or they feel the web detection apparatus is a nuisance that merely interfers with the operation of the machinery. They may think they have better visual control over the operation of the apparatus and can shut down the machinery if a web break occurs. Of course, if they are not present when a web break occurs or if they are at the opposite end of the machinery where a break occurs, it may have the usual damaging consequences.

Accordingly, it is an object of the present invention to provide an improved web monitoring and control apparatus which has many desirable attributes when used in conjunction with web handling machinery.

Another object of the present invention is to provide an improved system that can include a digital read-out which identifies the location of the detected web break in those web handling machines which require a considerable number of monitoring stations.

Still another object of the present invention is to provide a system of the foregoing type which is automatically activated when the web handling machinery is started and reaches a predetermined operating speed.

A more detailed object of the present invention is to provide a system of the foregoing type which can provide a warning signal that the detectors are becoming dirty and that they should be cleaned before a false web break indication is produced.

Other objects and advantages will become apparent upon reading the following detailed description, while referring to the attached drawings in which:

FIG. 1 is a functional block diagram of the apparatus of the present invention;

FIG. 2 is a detailed electrical schematic diagram of one embodiment of a portion of the present invention, particularly illustrating the automatic arming or activation control circuitry, the web break detecting and control circuitry as well as the dirty lens warning circuitry;

Figure 3:
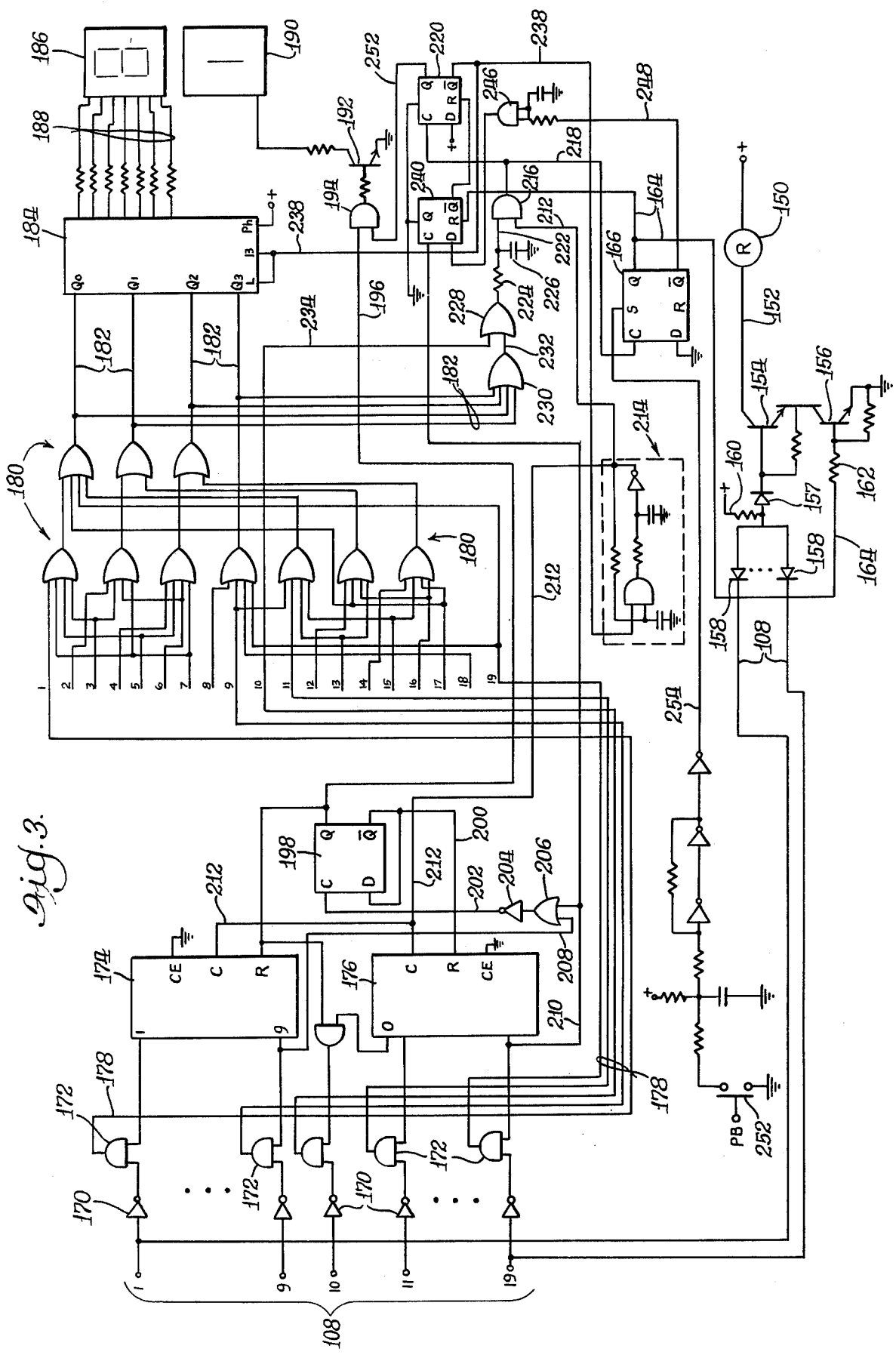
FIG. 3 is an electrical schematic diagram illustrating the digital read-out circuitry and web machinery stop interface circuitry of the present invention.

Turning now to the drawings, and particularly FIG. 1, a web 10 is shown to be vertically oriented for convenience and is intended to be a segment of a generally continuous web that is moved by a web handling machine. An infrared emitter 12 is positioned adjacent the web, as is an infrared receiver and amplifier 14. The infrared emitter and receivers may be conveniently packaged in the single enclosure that is suitably mounted adjacent the web, preferably so that the angle $\theta$ between the incidence beam 16 relative to a line perpendicular to the plane of the web and also the angle $\theta$ between the same line and the reflected beam 18 are relatively narrow, i.e., it is within the range of about 5° to 10° and preferably about 7°. When a relatively small angle $\theta$ is used, together with the circuitry incorporated herein, the distance d between the emitter and receiver package and the surface of the web can be within the range of about 1½ inches to about 6 inches, the greater distance being preferred, so that flutter of the web, i.e., the movement of the web toward and away from the receiver, will not appreciably affect the operation of the apparatus. It should be understood that when the web breaks, it will not present a reflecting surface to the infrared energy and the indication of a break will be produced. However, when the web flutters or has slack in it during operation of the machinery, a larger angle $\theta$ has the tendency to create false indications of a break.

The infrared emitter 12 is adapted to intermittently produce the infrared energy, preferably at a frequency of about 2000 Hertz. The energy is detected by the receiver 14 and is amplified and forwarded to an automatic arming control 20 which is in itself controlled by a web machinery speed indicator 22 that is interlocked with the machinery and provides a control signal to the automatic arming control 20 when the machinery reaches a predetermined speed, i.e., about 10% of its operating speed, for example. Once the web machinery exceeds the 10% speed value, the automatic arming control activates the apparatus so that the web is then monitored and the signal from the receiver and amplifier 14 is applied to the web break detector and control circuitry 24. The automatic arming control also produces a web present indicator signal on line 26 extending to a web present indication light 28 and the automatic arming control 20 also provides a signal on line 30 to an indicator light 32 which indicates whether the particular detector circuitry is activated or not.

It should be appreciated that there may be several locations that are not to be monitored and a large number of monitoring stations having the emitters and detectors and associated circuitry. In a large printing press, for example, there may be up to 20 or more of such monitoring stations. During start up of the web handling machinery, web machinery speed indicators 22 at each location control the automatic arming control circuitry 20 for each monitoring station and activate portions of the apparatus as the entire web machinery is brought up to speed. Thus, the apparatus of the present invention is adapted to incrementally monitor each stage of the machinery and automatically arm each detector apparatus and thereby insure adequate control of the entire machinery.

In accordance with another aspect of the present invention, the web break detector control circuitry 24 also incorporates dirty lens warning circuitry which effectively provides a warning indication to an indicator 36 via line 34 when the receiver 14 lens becomes sufficiently soiled that the level of the signal is reduced (when the web is present of course) and thereby increases the likelihood that a false web break indication will be generated. If the web break detector and control circuitry 24 does in fact receive a signal indicating that a break in the web has occurred, the identity of the detector is sent to a digital read-out 40 via line 38. The read-out 40 is needed generally only when a large number of monitoring stations are used and is preferably at a location where the machinery controls are so that the location can be quickly determined by the operator. It should be appreciated that a digital read-out would only be provided in a single or at most a few locations and would not be a part of each monitoring station. If a break is detected, web machinery stop interface circuitry 42 will shut down the machinery, typically by dropping out a relay or otherwise activating circuitry which is interconnected with the actual electrical power to the web handling machinery.

Specific circuitry that can be used to carry out the operation of the block diagram shown in FIG. 1 is shown in FIGS. 2 and 3, with the majority of the circuitry being specifically illustrated in FIG. 2, the web machinery stop interface circuitry 42 and the digital read-out circuitry 40 being shown in FIG. 3. Referring initially to FIG. 2, an infrared energy emitting diode 50 is shown with its anode being connected to an oscillator (not shown) of conventional design with energizes the light emitting diode at a predetermined frequency, preferably on the order of about 2000 Hertz. The infrared receiver includes a phototransistor 52 that is adapted to receive the infrared energy from the web after having been reflected therefrom and the infared energy places the phototransistor 52 into conduction, the phototransistor being operated in the common emitter mode, the transistor having a by-pass capacitor 54 connected between its emitter and ground. The output of the phototransistor 52 is fed to a band pass amplifier 56. The signal is applied to the amplifier 56 via line 58 and a pair of capacitors 60 and 62 attenuate the signal at a rate of 40 dB per decade at frequencies lower than 2000 Hertz while a capacitor 64 connected across output line 66 of the amplifier and one of the inputs effectively short circuits the amplifier for frequencies above 2000 Hertz. The output line 66 is then connected via another capacitor 70 to another amplifier 72 which performs the same low frequency attenuation, but the capacitor connected across the output and one of the inputs thereof is not present or needed since the requisite high frequency attenuation has been performed in the prior stage. The finally amplified signal appears on line 74 which has a potentiometer 76 connected to the base of a transistor 78 through a resistor 80. The transistor 78 has its collector connected to a Schmidt trigger 82 via a resistor 84 and line 86 and line 86 also is connected to a capacitor 88 which is in turn connected to ground. The emitter of transistor 78 is connected directly to ground. Supply voltage on line 90 drives the Schmidt trigger and provides voltage to the collector of the transistor 78 via a resistor 92. The resistor 84 and capacitor 88 comprise an integrator and the potentiometer 76 is adjustable to adjust the drive voltage to the base of the transistor 78.

During operation, the transistor 78 only conducts during the positive alternation of the input and when it is conducting, it provides a drain or discharge path for the capacitor 88 through the resistor 84 and the collector-to-emitter circuit of the transistor 78. During the negative alternation of the signal, the transistor 78 is not conducting so that the positive voltage on line 90 charges the capacitor 88 through the resistor 92 and resistor 84 and thereby charges the capacitor a small amount. When the voltage on capacitor 88 is below 5 volts, the Schmidt trigger 82 indicates that the web is present. If a web break occurs, the phototransistor 52 will be switched off which will result in the transistor 78 being switched off and the capacitor 88 will be charged to a voltage above about 10 volts and the Schmidt trigger will change state indicating that no web is present. The different states of the Schmidt trigger occur on output line 94 as well as on line 96. Thus, during normal operation when a web is present, the transistor 78 will be switched on and off during positive and negative alternations. Because the discharging occurs at a faster rate than charging, the capacitor 88 will be essentially discharged after preferably about 15 cycles so that the voltage on line 86 controlling the Schmidt trigger will be less than about 5 volts and thereby indicate that a web is present. The line 94 is preferably connected to an indicator light, such as a light emitting diode circuit, while line 96 extends through a diode 98 and line 100 to the D input of a flip-flop 102 which has its $\bar{Q}$ output 104 connected to an AND gate 106 (actually an OR gate serving an AND gate function), with the other input to the AND gate 106 being provided by the line 100. When a web is present, line 100 will be high and will be switched low when a web break is detected. A low voltage on line 100 produces a low on line 108 that extends to the web machinery stop interface circuitry, provided that the apparatus is armed or activated as will be hereinafter explained.

In accordance with an important aspect of the present invention, the automatic arming control is shown near the lower portion of FIG. 2 and has the lines 110 and 112 connected to a web machinery speed indicating apparatus that is adapted to provide a high voltage when the speed of the web handling machinery exceeds about 10% of its operating speed. When the speed is below the 10% value, the voltage on line 110 is zero and above it, approximately 120 volts, although the voltage level may vary depending upon the control voltage of the machinery itself. In any event, the speed indicating circuitry is of conventional design and may comprise microswitches or the like. When the voltage appears across lines 110 and 112, a light emitting diode portion 114 of an opto-oscillator 116 is activated and a phototransistor 118 is switched into conduction which provides a discharge path for a capacitor 120 which then provides a low level on the collector which is connected by line 122 to an inverter 124 so that the output of the inverter on line 126 goes high when the machine speed exceeds 10%, effectively clocking the flip-flop 102, thereby arming the apparatus so that a web break detection low level on line 100 will satisfy the gate 106 and result in the desired low signal on line 108. The input to the flip-flop 102 is also connected via an inverter 130 and line 132 to a web present indicator and line 132 is therefore high when the web is being detected. The $\overline{Q}$ output of the flip-flop 102, i.e., line 104 is also connected to an inverter 134 and line 136 to the head defeat indicator 32 and line 136 is low when the machine speed is less than 10% and is high when it is not, thereby energizing an indicator when the apparatus is not armed.

In accordance with another aspect of the present invention, the dirty lens indication circuitry will now be described in conjunction with FIG. 2 and comprises a comparator 140 having one input connected by line 86 and thereby applies the voltage level present on the capacitor 88 to one input of the comparator 140, the other input of which is supplied through a potentiometer 142 connected to the positive voltage via line 90. As previously mentioned, when the voltage on line 86 is less than about 5 volts, then the web is being detected as being present. When the voltage on line 88 exceeds 10 volts, then the Schmidt trigger indicates that the web has broken. By adjusting the potentiometer 142 to a value between 5 and 10 volts, the presence of a soiled or dirty lens to the phototransistor 52 can be detected and when the voltage exceeds the preselected value, which may be about 7½ volts, a low signal on line 34 extending to an indicator can provide a warning that the lens is becoming dirty and should be cleaned before the apparatus generates a false web break signal and shuts down the web handling machinery. In this regard, line 34 can extend to a separate indicator conveniently located at the side of the machinery and can also extend to a digital read-out similar to that read-out 40 that will be hereinafter described in detail. By providing a digital read-out at the operators control console, the operator will be alerted to the identity and location of monitoring stations that have detectors that are becoming dirty.

Turning now to the digital read-out and web handling machine stop interface circuitry and referring to FIG. 3, the web handling machinery stop interface may control a relay coil 150 that controls the power to the machinery or which can be interfaced with other control circuitry associated with the operation of the machinery. In any case, the relay coil 150 is operative to permit the web machinery to operate in a normal manner when the coil is energized and when it is de-energized, will result in the machinery being shut down. The coil 150 is connected via line 152 to the collector of a transistor 154, the emitter of which is connected to the collector of a second transistor 156 and its emitter is connected to ground. Thus, when both transistors are in conduction, the coil 150 will be energized. While the use of a digital read-out display may be desirable for many applications, the shutting down of the web machinery will occur even if the digital read-out aspect of the invention is not included. In this regard, the base of transistor 154 is connected via diode 157 to a plurality of additional diodes 158, each of which is in turn connected to the detector circuit of one of the monitoring stations such as the one described and illustrated in FIG. 2. Thus, lines 108 from the FIG. 2 extend to the circuitry of FIG. 3 and are connected to the diodes 158, with any one of the lines being low due to the detection of a web break causing a ground path for the positive voltage applied to resistor 160. When this occurs, then the positive voltage will not be applied through diode 157 to the base of transistor 154 and it will be turned off which will cause the relay coil 150 to be de-energized. In a similar manner, the transistor 156 has its base connected via resistor 162 and line 164 to the Q output of a flip-flop 166 which is normally high. Through the operation of the display circuitry, if such is included in the particular application, will result in transistor 156 being shut off which will also have the effect of de-energizing the relay coil 150. The two transistors 154 and 156 thereby operate in a redundant fashion in the event that both are included and insure that the web machinery will be stopped if a web breaks.

Referring again to FIG. 3, each of the multiple inputs 108 shown to the left are separately numbered and indicate an input from separate and distinct web monitoring stations, such as the one shown in FIG. 2. Each of the inputs is connected to inverters 170 which are connected to one input of AND gates 172, the other input of which is supplied by one of two ripple counters 174 or 176. The output of each AND gate 172 is connected by a corresponding line 178 to a plurality of OR gates 180 which ultimately produce binary coded decimal signals on four lines 182 which comprise the coded inputs to a driver circuitry 184 for driving a seven segment display device 186 via the seven lines 188. Since the number of input lines 108 in the embodiment shown in FIG. 3 number a total of 19, it should be appreciated that only one complete seven segment display 186 is required and that if the monitoring station identity is a double digit number, only the number 1 need be energized. Accordingly, a "one" indicator 190 is provided which is driven by transistor 192 and controlled through AND gate 194 and line 196 originating at the Q output of a flip-flop 198. The flip-flop 198 has its Q output connected via line 196 to the ring counter 174 and its $\overline{Q}$ output connected to the ring counter 176 via line 200. The flip-flop 198 is clocked by line 202 via inverter 204 and OR gate 206 which is connected to the nine output of counter 176 via line 208 and to the 19 output of counter 176 (actually the 9 output thereof) by line 210. Lines 208 and 210 effectively clock the flip-flop 198 so that the ring counters 174 and 176 are alternately reset so that they sequence through all inputs 1 through 19 as is desired.

The counters 174 and 176 are clocked via line 212 which extends from a stepper clock indicated generally at 214. The output on line 212 also extends to AND gate 216, the output of which appears on line 218 that extends to flip-flop 220 as well as to the clock input of the flip-flop 166. In addition to input line 212, the gate 216 has an input line 222 that is supplied through a delay circuit comprising resistor 224 and capacitor 226. The delay circuit is connected to OR gate 228 which has one input from an OR gate 230 via line 232 and a second input supplied by the number 10 input via line 234. The inputs to the OR gate 230 are supplied by lines 182 so that if any number is appearing on lines 182 and line 234, which indicates that the infrared energy has not been detected and that a web break has therefore occurred, then OR gates 230 and 228 will be satisfied which will satisfy input line 222 to the AND gate 216 and on the next clock pulse, AND gate 216 will be satisfied and will clock the flip-flop 220 as well as flip-flop 166. The flip-flop 166 will then have its Q output line 164 low which will cause transistor 156 to be shut off and will drop out relay 150 and shut down the machinery. Thus, any number appearing on lines 182 and 234 will result in the machinery being shut down.

Before the display indicates which monitoring station detected the web break, the driver 184 must be loaded and unblanked which is performed by a signal on line 238 which obtains from the $\overline{Q}$ output of flip-flop 220. The flip-flop 240 is clocked by the last digit from the ripple counter 176 so that after it has sequenced through the entire sequence of inputs, it will clock the flip-flop 240, the $\overline{Q}$ output of which is connected to the reset of flip-flop 220 via line 242. The D input to the flip-flop 240 is applied via line 244 through a delay and buffer 246 which is connected via line 248 to the $\overline{Q}$ output of flip-flop 166. When flip-flop 166 is clocked and shuts down the web handling machinery, the line 248 goes high and the combination of the flip-flops 240 and 222 cause the ripple counter to be again sequenced and when the input is reached which has the signal indicating that infrared energy has not been detected will result in the driver 184 being unblanked and loaded via line 238 from the flip-flop 220 which will result in the digital display being activated. The Q output of flip-flop 220 is connected via line 252 to the AND gate 194 and permits the display 190 to be energized if the monitoring station detecting the break is from station numbers 10 through 19. Line 238 also extends to the clock 214 and provides an interrupt for the clock once the display number that is to be loaded so that sequencing of the ripple counter will then be stopped and the display will be maintained. After the problem which caused the shutting down of the machinery has been corrected, a push button 252 may be activated which sets flip-flop 166 via line 254 and the setting of this flip-flop effectively resets flip-flops 240 and 220 which enables the clock 240 to be restarted and resume normal operation of the apparatus.

From the foregoing, it should be appreciated that an improved monitoring and control system has been shown and described which is particularly adapted for use with web handling machinery of the type which handles a generally continuously moving web which may be subject to breakage. The monitoring and control apparatus of the present invention has many desirable attributes, including automatic arming or activation of the apparatus upon start up of the web handling machinery. This eliminates the uncertainty and occasional unreliability of operators who sometimes view such systems as a nuisance and thereby insure that the web handling machinery is being monitored anytime it is in use. Moreover, in those applications where the web handling machinery is extensive and covers a large area, where it is desirable, if not necessary to have a large number of monitoring stations, the apparatus of the present invention can provide a visual read-out of the location where a web breakage has occurred so that it can be attended to with a minimum of down time for the machinery. The apparatus incorporates redundancy in its design to minimize the probability that the machinery will not be shut down in the event that a web break is detected. Moreover, in those applications where the web handling machinery experiences considerable dust and ink, such as occurs in an offset printing press or with newspaper printing press, the apparatus incorporates circuitry for providing a warning when the detectors are beginning to become dirty prior to them reaching a level where they will automatically shut down the machinery. Thus, the providing of a warning indication alerts the operators so that they can clean the detectors before the apparatus misinterprets the absence of the reflected infrared energy and shuts down the machinery.

It is of course understood that although preferred embodiments of the present invention have been illustrated and described, certain modifications, equivalents and substitutions thereof will become apparent to those skilled in the art and, accordingly, the scope of the present invention should be defined only by the appended claims and equivalents thereof.

Various features of the invention are set forth in the following claims.

What is claimed is:

1. Apparatus for monitoring a web of material being moved by web handling machinery having operating control means, said apparatus having at least one web monitoring station for monitoring the web adjacent thereto, each web monitoring station comprising:
    means for intermittently emitting infrared energy toward the web at a predetermined frequency and angle relative to a line generally perpendicular to the plane of the web;
    means for detecting infrared energy reflected from the web, and for generating electrical signals that selectively indicate the presence and absence of reflected infrared energy;
    means responsive to said electrical signals indicating the absence of said energy for interacting with the operating control means of the machinery to stop the web handling machinery;
    means for automatically disabling said detecting and generating means when said web handling machinery is operating below a predetermined speed and for enabling the same when the operating speed exceeds said predetermined speed; and,
    means for monitoring the level of said electrical signals being generated by said detecting and generating means and for producing warning signals in response to the energy being detected being less than a desired value when reflected energy is being detected, thereby providing a warning that said detection means may be becoming dirty.

2. Apparatus as defined in claim 1 including two or more of said monitoring stations, said apparatus further including display means for identifying the monitoring station that produces the electrical signals indicating the absence of reflected infrared energy.

3. Apparatus as defined in claim 2 wherein said display means comprises means for visually generating the identifying number of the monitoring station that produces the electrical signals indicating the absence of reflected energy.

4. Apparatus as defined in claim 3 further including manually operable means for resetting said display means after said web handling machinery has been stopped.

5. Apparatus as defined in claim 1 wherein said detection means produces an alternating polarity signal when said reflected energy is detected and said generating means includes circuit means that alternately charges and discharges a capacitor during alternate polarity alternations, the voltage level exceeding a first value indicating the absence of said reflected detected energy, the level being below a second value indicating the presence of reflected energy due to the presence of the web, said first and second values being separated from one another and said desired value being intermediate said first and second values.

6. Apparatus as defined in claim 5 wherein said circuit means comprises a Schmidt trigger biased so that said first value is approximately 10 volts, said second value is approximately 5 volts.

7. Apparatus for monitoring a moving web of material being moved by web handling machinery having operating control means, said apparatus being adapted to cause said machinery to stop moving the web in response to the detection of a break of the web, said apparatus including one or more monitoring stations positioned adjacent the web, each of said stations comprising:
   first means for intermittently emitting infrared energy toward said web at a predetermined frequency;
   second means positioned relative to said web for detecting infrared energy reflected from said web when said web is present, said second means having a lens means through which said infrared energy passes, said second means producing electrical signals in response to the detection of the presence or absence of said infrared energy;
   third means responsive to said electrical signals for generating other signals for application to said operating control means for shutting down said machinery when said electrical signals are indicative of the absence of said infrared energy being detected;
   fourth means responsive to said electrical signals for generating warning signals when the level of said electrical signals drop below a predetermined value when infrared energy is being detected;
   fifth means for selectively enabling and disabling said second means in response to movement of said web by said web handling machinery, said second means being normally disabled when said web handling machinery is operating below a predetermined speed and automatically enabled when the operating speed exceeds a predetermined speed.

8. Apparatus as defined in claim 7 wherein said predetermined speed is about 10 percent of the normal operating speed.

9. Apparatus as defined in claim 7 wherein said apparatus includes a plurality of said web monitoring stations, and further includes means for providing a visual display of the identification of a monitoring station that has detected the absence of reflected infrared energy.

10. Apparatus as defined in claim 9 wherein said visual display providing means provides a numerical visual display identifying the identifying number of said web monitoring station that has detected the absence of reflected infrared energy.

11. Apparatus as defined in claim 7 wherein said second means produces an alternating polarity electrical signal when said reflected energy is detected and includes circuit means that alternately charges and discharges a capacitor during alternate polarity alternations of said signal, the voltage level exceeding a first value being indicative of the absence of said reflected detected energy, the level of said signal being below a second value indicating the presence of reflected infrared energy, said first and second levels being separated from one another, said desired value being intermediate said first and second values.

12. Apparatus as defined in claim 11 wherein said circuit means comprises a Schmidt trigger.

* * * * *